US009060887B2

(12) United States Patent
Hartley et al.

(10) Patent No.: US 9,060,887 B2
(45) Date of Patent: *Jun. 23, 2015

(54) FENESTRATED STENT GRAFTS

(75) Inventors: David Ernest Hartley, Wannanup (AU); John Lennon Anderson, Bellevue Heights (AU); Michael Lawrence-Brown, City Beach (AU)

(73) Assignee: Cook Medical Technologies LLC, Bloomington, IN (US)

(*) Notice: Subject to any disclaimer, the term of this patent is extended or adjusted under 35 U.S.C. 154(b) by 536 days.

This patent is subject to a terminal disclaimer.

(21) Appl. No.: 12/228,453

(22) Filed: Aug. 13, 2008

(65) Prior Publication Data
US 2008/0312732 A1 Dec. 18, 2008

Related U.S. Application Data

(62) Division of application No. 10/962,765, filed on Oct. 12, 2004, now Pat. No. 7,413,573.

(60) Provisional application No. 60/510,241, filed on Oct. 10, 2003, provisional application No. 60/529,346, filed on Dec. 12, 2003.

(51) Int. Cl.
*A61F 2/06* (2013.01)
*A61F 2/856* (2013.01)
(Continued)

(52) U.S. Cl.
CPC . *A61F 2/856* (2013.01); *A61F 2/07* (2013.01); *A61F 2002/061* (2013.01); *A61F 2002/067* (2013.01); *A61F 2002/075* (2013.01);
(Continued)

(58) Field of Classification Search
CPC ..... A61F 2/856; A61F 2/07; A61F 2002/061; A61F 2002/067; A61F 2002/075; A61F 2002/821; A61F 2220/0075
USPC ...................... 623/1.13–1.16, 1.18, 1.3–1.32, 623/1.35–1.36, 1.22–1.26, 2.1; 606/153
See application file for complete search history.

(56) References Cited

U.S. PATENT DOCUMENTS

| 4,902,508 A | 2/1990 | Badylak et al. |
| 5,387,235 A | 2/1995 | Chuter |

(Continued)

FOREIGN PATENT DOCUMENTS

| WO | WO98/22158 | 5/1998 |
| WO | WO98/53761 | 12/1998 |

(Continued)

OTHER PUBLICATIONS

T. Huynh, Remodeling of an acellular collagen graft into a physiologically responsive neovessel, Nature Biotechnology, Nov. 1999, p. 1083-1086, vol. 17, issue 11, Nature America Inc.

*Primary Examiner* — Thomas McEvoy
(74) *Attorney, Agent, or Firm* — Brinks Gilson & Lione

(57) ABSTRACT

A stent graft (1) including a tubular wall (3) with at least one fenestration (40) including a peripheral (37) reinforcement around at least part of the fenestration. There can also be a tubular extension (15). The side arm includes a stent (19) and a cover (17) and extends from and is in fluid communication with the fenestration and the stent graft. The stent may be a self expanding stent. The ring and/or tubular extension provides better support and sealing for an extension arm. The fenestration (40) can be circular or if towards the ends of the stent graft may be in the form of a U-shape (50) with an open end.

11 Claims, 8 Drawing Sheets

(51) Int. Cl.
  *A61F 2/07* (2013.01)
  *A61F 2/82* (2013.01)
  *A61F 2/89* (2013.01)

(52) U.S. Cl.
  CPC ... *A61F2002/821* (2013.01); *A61F 2250/0039* (2013.01); *A61F 2/89* (2013.01); *A61F 2220/0075* (2013.01); *A61F 2230/0078* (2013.01)

(56) References Cited

U.S. PATENT DOCUMENTS

| | | | |
|---|---|---|---|
| 5,591,230 A * | 1/1997 | Horn et al. | 623/1.17 |
| 5,617,878 A | 4/1997 | Taheri | |
| 5,653,743 A | 8/1997 | Martin | |
| 5,709,713 A | 1/1998 | Evans et al. | |
| 5,711,969 A | 1/1998 | Patel et al. | |
| 5,720,776 A | 2/1998 | Chuter et al. | |
| 5,733,337 A | 3/1998 | Carr, Jr. et al. | |
| 5,755,778 A | 5/1998 | Kleshinski | |
| 5,769,882 A | 6/1998 | Fogarty et al. | |
| 5,782,904 A | 7/1998 | White et al. | 623/1 |
| 5,885,619 A | 3/1999 | Patel et al. | |
| 5,906,640 A | 5/1999 | Penn et al. | |
| 5,921,995 A | 7/1999 | Kleshinski | |
| 5,955,110 A | 9/1999 | Patel et al. | |
| 5,961,548 A | 10/1999 | Shmulewitz | |
| 5,968,096 A | 10/1999 | Whitson et al. | |
| 5,984,955 A | 11/1999 | Wisselink | |
| 6,056,775 A | 5/2000 | Borghi et al. | |
| 6,077,296 A * | 6/2000 | Shokoohi et al. | 623/1.11 |
| 6,099,558 A | 8/2000 | White et al. | 623/1.16 |
| 6,187,033 B1 | 2/2001 | Schmitt et al. | |
| 6,203,568 B1 * | 3/2001 | Lombardi et al. | 623/1.13 |
| 6,206,931 B1 | 3/2001 | Cook et al. | |
| 6,210,429 B1 | 4/2001 | Vardi et al. | |
| 6,221,102 B1 * | 4/2001 | Baker et al. | 623/1.36 |
| 6,261,273 B1 | 7/2001 | Ruiz | |
| 6,287,315 B1 * | 9/2001 | Wijeratne et al. | 606/108 |
| 6,287,330 B1 * | 9/2001 | Johansson et al. | 623/1.13 |
| 6,325,826 B1 | 12/2001 | Vardi et al. | |
| 6,334,867 B1 | 1/2002 | Anson | |
| 6,344,052 B1 * | 2/2002 | Greenan et al. | 623/1.1 |
| 6,395,018 B1 * | 5/2002 | Castaneda | 623/1.13 |
| 6,409,750 B1 | 6/2002 | Hyodoh et al. | |
| 6,428,565 B1 | 8/2002 | Wisselink | |
| 6,524,335 B1 | 2/2003 | Hartley et al. | |
| 6,558,418 B2 * | 5/2003 | Carpentier et al. | 623/2.14 |
| 7,011,679 B2 * | 3/2006 | Lauterjung | 623/1.35 |
| 7,105,020 B2 | 9/2006 | Greenberg et al. | 623/1.35 |
| 7,537,606 B2 | 5/2009 | Hartley et al. | 623/1.11 |
| 2003/0088305 A1 | 5/2003 | Van Schie et al. | |
| 2003/0120332 A1 | 6/2003 | Hartley et al. | |
| 2003/0233140 A1 | 12/2003 | Hartley et al. | |
| 2004/0073289 A1 | 4/2004 | Hartley | |
| 2004/0082990 A1 | 4/2004 | Hartley | |
| 2004/0098079 A1 | 5/2004 | Hartley et al. | |
| 2004/0106978 A1 | 6/2004 | Greenberg et al. | |
| 2004/0215327 A1 * | 10/2004 | Doig et al. | 623/1.16 |
| 2004/0225349 A1 * | 11/2004 | Thistle et al. | 623/1.16 |

FOREIGN PATENT DOCUMENTS

| | | |
|---|---|---|
| WO | WO99/29262 | 6/1999 |
| WO | WO03/034948 | 5/2003 |
| WO | WO03/053287 | 7/2003 |
| WO | WO03/101518 | 12/2003 |
| WO | WO2004/002365 | 1/2004 |
| WO | WO2004/002370 | 1/2004 |
| WO | WO2004/017867 | 3/2004 |
| WO | WO2004/017868 | 3/2004 |
| WO | WO2004/028399 | 4/2004 |

* cited by examiner

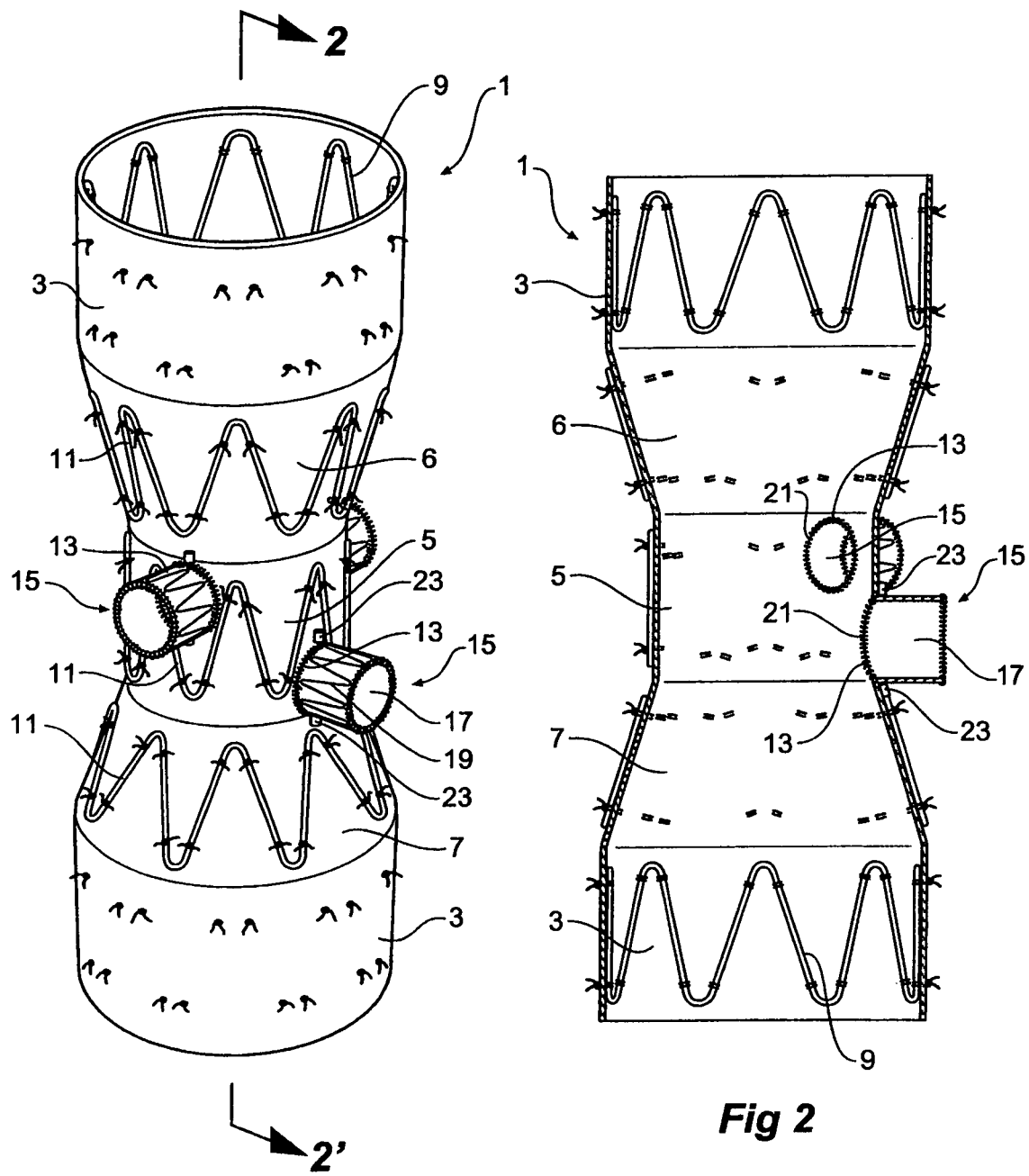

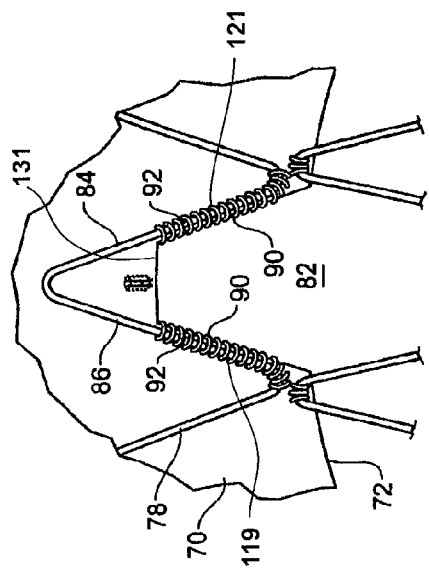
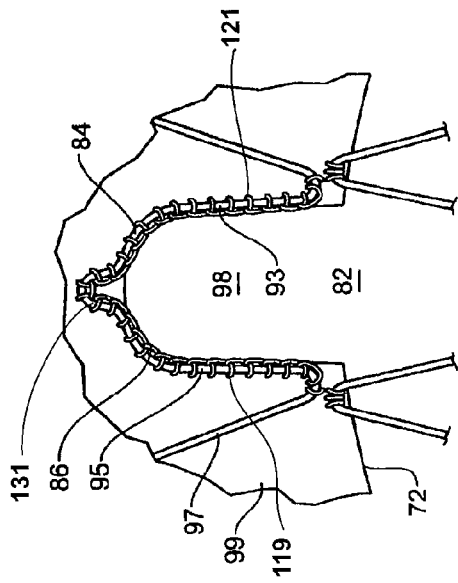
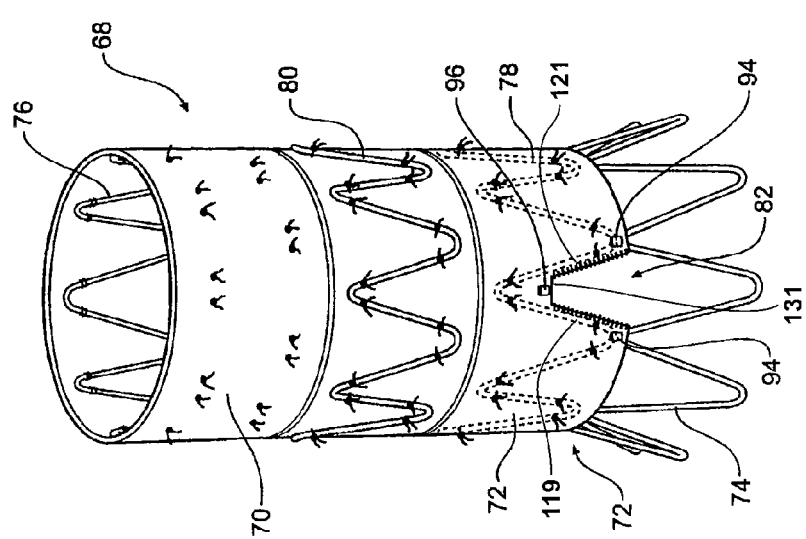

US 9,060,887 B2

FENESTRATED STENT GRAFTS

CROSS-REFERENCE TO RELATED APPLICATIONS

This application is a divisional of Ser. No. 10/962,765, filed Oct. 12, 2004, now U.S. Pat. No. 7,413,573, which claims priority of provisional application Ser. No. 60/510,241 filed Oct. 10, 2003 and provisional application Ser. No. 60/529,346 filed Dec. 12, 2003, which are incorporated by reference in their entirety.

TECHNICAL FIELD

This invention relates to a stent graft adapted for endovascular deployment and in particular to a fenestrated stent graft.

BACKGROUND OF THE INVENTION

In our earlier patent application published as WO 99/29262 there was disclosed a stent graft including at least one fenestration to enable an extension leg graft to be extended from a main stent graft in an internal lumen through the fenestration to have the extension leg or arm graft extend into a branch vessel of the lumen. Such a situation may exist in the aorta with renal arteries extending from the aorta. When there is an aneurysm in this region which includes the junction of the aorta with the renal arteries then it is desirable to not only have a main graft which spans the aneurysm but also extension legs or arms which extend from the main graft into the renal or other arteries.

A simple fenestration does not necessarily give a fully reliable support and sealing surface for the extension leg graft and it is the object of this invention to improve the ability for support and sealing of an extension leg or arm grafts into a main graft.

SUMMARY OF THE INVENTION

In one form, therefore, the invention is said to reside in a stent graft having a tubular wall and at least one fenestration in the tubular wall, the or each fenestration including a resilient material around at least a portion of the periphery thereof to provide dimensional stability to the fenestration.

Preferably the resilient material may be selected from Nitinol, stainless steel or elastomeric material and may be in the form of a spring, expandable ring such as a slip ring or a portion of resilient wire.

In one form the resilient material around the periphery may be in the form of a ring.

Preferably the ring includes at least two turns of wire and preferably the terminal ends of the wire of the ring are provided with a loop so that the wire does not present a pointed end of wire which could damage a vessel.

Alternatively, the ring may be a ring of a resilient material such as an elastomer. The elastomer may for instance be silicone elastomer.

Where the fenestration is adjacent an end of the stent graft the fenestration may be in the form of a scallop which is open at one side. The resilient material around the periphery may be in the form of a U-shape and during deployment may assist with opening up of the fenestration so that a vessel behind the fenestration can be catheterized.

In another embodiment of a fenestration in the form of a scallop provided at the distal or proximal end of the stent graft, it may have struts of self expanding stents acting as resilient peripheral reinforcement around a portion of the fenestration. When the stent expands upon deployment, the struts spread apart thereby opening up the fenestration.

The scallop may be at the proximal or distal end of a stent graft. For instance, when deploying a stent graft extending from the thoracic arch, a fenestration may be provided to prevent the coeliac artery being occluded. As with all embodiments, radiopaque or MRI opaque markers may be used to define the periphery of the fenestration.

When deploying a stent graft into the lower aorta in the region of the aortic bifurcation, it may be desirable to provide a scalloped fenestration at the proximal end of the stent graft to avoid occluding the renal arteries or the superior mesenteric artery. Where these arteries are close together the scalloped fenestration may be of such a size that it extends over more than one of the openings to the arteries.

The U-shape of resilient material can be a Nitinol or a stainless steel wire or may be a portion of an elastomeric material such as a silicone elastomer.

The fenestration may be surrounded by radiopaque markers to assist with visualisation by suitable radiographic techniques. Alternatively there may be included in or associated with the resilient material a gold or other heavy metal wire or band to provide the necessary visualisation.

In one embodiment the fenestration may include a tubular extension between the tubular wall and the ring.

The tubular extension may include a self expanding stent and an associated lining or covering of a biocompatible graft material.

In an alternative form the invention is said to reside in a stent graft having at least one fenestration, the fenestration including a tubular extension, the side arm including a stent and extending from and in fluid communication with the fenestration and the tubular wall.

Preferably the tubular extension includes an associated lining or covering of a biocompatible graft material. By this arrangement the inner cylindrical surface of the tubular extension provides a larger support and sealing surface between the fenestration in the main graft and an outer cylindrical surface of a side branch stent graft which has been deployed through the fenestration.

Preferably the stent in the tubular extension is a self expanding stent which may be Nitinol™ or stainless steel. Alternatively the stent in the tubular extension may be a balloon expandable stent.

In one form the stent may be in the form of a well-known Gianturco style zig zag Z stent. Alternatively the stent may be a Nitinol self expanding stent of the type known as a ZILVER™ stent sold by Cook Incorporated, Bloomington, Ind.

The bio-compatible graft material may be either on the inside or the outside of the stent or there may be a cover which extends over both the inside and the outside of the stent on the tubular extension.

There may be further included a ring of a resilient material around the periphery at the terminal end of the tubular extension to provide dimensional stability to the tubular extension to assist with sealing. The ring may be formed from one or more and preferably two or more circular turns of Nitinol or stainless steel wire and preferably have a loop at each of its ends to prevent the wire from presenting a sharp end which might protrude through the graft material and pierce a lumen wall.

The bio-compatible material may be dacron, Thoralon™, expanded polytetrafluoroethylene or other synthetic biocompatible material.

While Dacron, expanded polytetrafluoroethylene (ePTFE), or other synthetic biocompatible materials can be used to fabricate the coverings for the stent graft and the tubular extension, a naturally occurring biomaterial, such as collagen, is highly desirable, particularly a specially derived collagen material known as an extracellular matrix (ECM) material, such as small intestinal submucosa (SIS) commercially available from Cook Biotech, West Lafayette, Ind. Besides SIS, examples of ECM's include pericardium, stomach submucosa, liver basement membrane, urinary bladder submucosa, tissue mucosa, and dura mater.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated 28 May 1998, which is the published application of PCT/US97/14855. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. Animal data show that the SIS used in grafts can be replaced by native tissue in as little as a month's time. In addition to xenogenic biomaterials, such as SIS, autologous tissue can be harvested as well. Additionally Elastin or Elastin-Like Polypetides (ELPs) and the like offer potential as a material to fabricate the graft to form a device with exceptional biocompatibility. Another alternative would be to use allographs such as harvested native tissue. Such tissue is commercially available in a cryopreserved state.

The tubular extension may be placed on a reduced diameter portion of the stent graft so that the overall diameter of the stent graft is not significantly affected.

For this specification the term 'tubular extension' in relation to the side arm, is intended to mean that the length of the tubular extension is substantially similar in order of magnitude to the diameter of the tubular extension. Hence for a tubular extension diameter of 6 millimetres the length may be in the range of 5 to 10 millimetres. Such a tubular extension diameter would be suitable for deploying an extension leg or arm graft for a renal artery extending from an aorta.

The stent graft may have a diameter of from 20 to 40 mm and a length of from 100 to 250 mm. The placement of the-fenestrations and the tubular extensions where required is dependant upon the particular body lumen and each set of fenestrations would normally be custom designed. The main stent graft may include a proximally extending uncovered stent to assist with retention within a body lumen such as an aorta.

The main stent graft in which the fenestration is provided may be one of the components of a composite graft.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

U.S. Pat. No. 6,524,335 and PCT Patent Publication No. WO 99/29262 entitled "Endoluminal Aortic Stents" disclose a fenestrated prosthesis for placement where there are intersecting arteries. This feature and other features disclosed in U.S. Pat. No. 6,524,335 and PCT Patent Publication No. WO 99/29262 could be used with the present invention and the disclosure of U.S. Pat. No. 6,524,335 and PCT Patent Publication No. WO 99/29262 is herewith incorporated in its entirety into this specification.

U.S. patent application Ser. No. 10/280,486, filed Oct. 25, 2002 and published on May 8, 2003 as U.S. Patent Application Publication No. US-2003-0088305-A1 and PCT Patent Publication No. WO 03/034948 entitled "Prostheses For Curved Lumens" discloses prostheses with arrangements for bending the prosthesis for placement into curved lumens. This feature and other features disclosed in U.S. patent application Ser. No. 10/280,486, and U.S. Patent Application Publication No. US-2003-0088305-A1 and PCT Patent Publication No. WO 03/034948 could be used with the present invention and the disclosure of U.S. Patent application Ser. No. 10/280,486, and U.S. Patent Application Publication No. US-2003-0088305-A1 and PCT Patent Publication No. WO 03/034948 is herewith incorporated in its entirety into this specification.

U.S. Provisional Patent Application Ser. No. 60/392,682, filed Jun. 28, 2002, U.S. patent application Ser. No. 10/447,406, filed May 29, 2003, and Published on Dec. 18, 2003, as U.S. Patent Application Publication No. US-2003-0233140-A1, and PCT Patent Publication No. WO 03/101518 entitled "Trigger Wires" disclose release wire systems for the release of stent grafts retained on introducer devices. This feature and other features disclosed in U.S. Provisional Patent Application Ser. No. 60/392,682, U.S. patent application Ser. No. 10/447,406, and U.S. Patent Application Publication No. US-2003-0233140-A1, and PCT Patent Publication No. WO 03/101518 could be used with the present invention and the disclosure of U.S. Provisional Patent Application Ser. No. 60/392,682, U.S. patent application Ser. No. 10/447,406, and U.S. Patent Application Publication No. US-2003-0233140-A1, and PCT Patent Publication No. WO 03/101518 is herewith incorporated in its entirety into this specification.

U.S. Provisional Patent Application Ser. No. 60/392,667, filed Jun. 28,2002, and U.S. patent application Ser. No. 10/609,846, filed Jun. 30, 2003, and Published on May 20, 2004, as US Patent Application Publication No. US-2004-0098079-A1, and PCT Patent Publication No. WO 2004/028399 entitled "Thoracic Deployment Device" disclose introducer devices adapted for deployment of stent grafts particularly in the thoracic arch. This feature and other features disclosed in U.S. Provisional Patent Application Ser. No. 60/392,667, U.S. patent application Ser. No. 10/609,846, and US Patent Application Publication No. US-2004-0098079-A1, and PCT Patent Publication No. WO 2004/

028399 could be used with the present invention and the disclosure of U.S. Provisional Patent Application Ser. No. 60/392,667, U.S. patent application Ser. No. 10/609,846, and US Patent Application Publication No. US-2004-0098079-A1, and PCT Patent Publication No. WO 2004/028399 is herewith incorporated in its entirety into this specification.

U.S. Provisional Patent Application Ser. No. 60/392,599, filed Jun. 28, 2002, and U.S. patent application Ser. No. 10/609,835, filed Jun. 30, 2003, and published on Jun. 3, 2004, as U.S. Patent Application Publication No. US-2004-0106978-A1, and PCT Patent Publication No. WO 2004/002370 entitled "Thoracic Aortic Aneurysm Stent Graft" disclose stent grafts that are useful in treating aortic aneurysms particularly in the thoracic arch. This feature and other features disclosed in U.S. Provisional Patent Application Ser. No. 60/392,599, U.S. patent application Ser. No. 10/609,835, and U.S. Patent Application Publication No. US-2004-0106978-A1, and PCT Patent Publication No. WO 2004/002370 could be used with the present invention, and the disclosure of U.S. Provisional Patent Application Ser. No. 60/392,599, U.S. patent application Ser. No. 10/609,835, and U.S. Patent Application Publication No. US-2004-0106978-A1, and PCT Patent Publication No. WO 2004/002370 is herewith incorporated in its entirety into this specification.

U.S. Provisional Patent Application Ser. No. 60/391,737, filed Jun. 26, 2002, U.S. patent application Ser. No. 10/602,930, filed Jun. 24, 2003, and PCT Patent Publication No. WO 2004/002365 entitled "Stent-Graft Fastening" disclose arrangements for fastening stents onto grafts particularly for exposed stents. This feature and other features disclosed in U.S. Provisional Patent Application No. 60/391,737, U.S. patent application Ser. No. 10/602,930, and PCT Patent Publication No. WO 2004/002365 could be used with the present invention and the disclosure of U.S. Provisional Patent Application Ser. No. 60/391,73, U.S. patent application Ser. No. 10/602,930, and PCT Patent Publication No. WO 2004/002365 are herewith incorporated in its entirety into this specification.

U.S. Provisional Patent Application Ser. No. 60/405,367, filed Aug. 23, 2002, U.S. patent application Ser. No. 10/647,642, filed Aug. 25, 2003, and PCT Patent Publication No. WO 2004/017868 entitled "Asymmetric Stent Graft Attachment" disclose retention arrangements for retaining onto and releasing prostheses from introducer devices. This feature and other features disclosed in U.S. Provisional Patent Application Ser. No. 60/405,367, filed Aug. 23, 2002, U.S. patent application Ser. No. 10/647,642, filed Aug. 25, 2003, and PCT Patent Publication No. WO 2004/017867 could be used with the present invention and the disclosure of U.S. Provisional Patent Application Ser. No. 60/405,367, filed Aug. 23, 2002, U.S. patent application Ser. No. 10/647,642, filed Aug. 25, 2003, and PCT Patent Publication No. WO 2004/017867 are herewith incorporated in its entirety into this specification.

U.S. patent application Ser. No. 10/322,862, filed Dec. 18, 2002 and published as Publication No. US2003-0120332, and PCT Patent Publication No. WO03/053287 entitled "Stent Graft With Improved Adhesion" disclose arrangements on stent grafts for enhancing the adhesion of such stent grafts into walls of vessels in which they are deployed. This feature and other features disclosed in U.S. patent application Ser. No. 10/322,862, filed Dec. 18, 2002 and published as Publication No. US2003-0120332, and PCT Patent Publication No. WO03/053287 could be used with the present invention and the disclosure of U.S. patent application Ser. No. 10/322,862, filed Dec. 18, 2002 and published as Publication No. US2003-0120332, and PCT Patent Publication No. WO03/053287 are herewith incorporated in its entirety into this specification.

U.S. Provisional Patent Application Ser. No. 60/405,769, filed Aug. 23, 2002, U.S. patent application Ser. No. 10/645,095, filed Aug. 23, 2003, and PCT Patent Publication Number WO 2004/017867 entitled "Composite Prostheses" discloses prostheses or stent grafts suitable for endoluminal deployment. These prostheses and other features disclosed in U.S. Provisional Patent Application Ser. No. 60/405,769, filed Aug. 23, 2002, U.S. patent application Ser. No. 10/645,095, filed Aug. 23, 2003, and PCT Patent Publication Number WO 2004/017867, could be used with the present invention and the disclosure of U.S. Provisional Patent Application Ser. No. 60/405,769, filed Aug. 23, 2002, U.S. patent application Ser. No. 10/645,095, filed Aug. 23, 2003, and PCT Patent Publication Number WO 2004/017867 are herewith incorporated in its entirety into this specification.

BRIEF DESCRIPTION OF THE DRAWING

This then generally describes the invention but to assist with understanding reference will now be made to the accompanying drawings which show a preferred embodiment of the invention.

In the drawings:

FIG. 1 shows one embodiment of a stent graft according to this invention;

FIG. 2 shows a cross section of the stent graft shown in FIG. 1 along the line 2-2';

FIG. 12 shows an alternative embodiment of a stent graft with a scalloped fenestration;

FIG. 13 shows a detailed internal view of the scalloped fenestration of FIG. 12;

FIG. 13A shows an internal view of an alternative arrangement of a scalloped fenestration;

DETAILED DESCRIPTION

Figure 3:
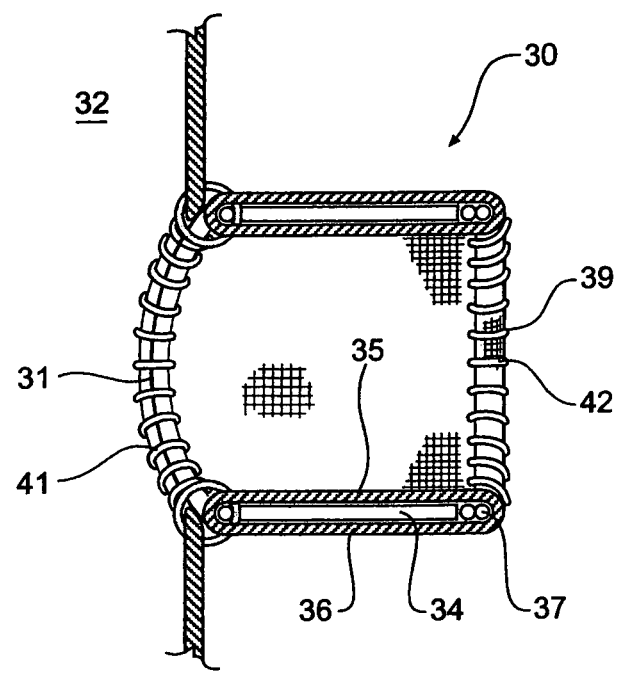
FIG. 3 shows a cross section through a tubular extension in one embodiment of the invention.

Now looking more closely at the drawings and in particular the embodiment shown in FIGS. 1 and 2 it will be seen that a main stent graft 1 comprises a tubular wall body portion 3 at proximal and distal ends of the stent graft 1 with a central reduced diameter portion 5 between the ends of the stent graft with tapered portions 6 and 7 extending from the tubular wall body portions 3 at each end to the central reduced diameter portion 5.

All of the tubular wall body portions, the tapered portions and the central portion are a biocompatible graft material such as Dacron, Thoralon™, expanded PTFE material or a naturally occurring biomaterial, such as an extracellular matrix, such as small intestinal submucosa or other suitable material or a combination of these materials.

Gianturco style zig zag Z stents 9 are provided inside the graft material of the tubular body portions 3 at each end and in between the ends Gianturco zig zag style Z stents 11 are provided on the tapering portions 6 and 7 and on the reduced diameter portion 5 outside of the graft material. There may be further Gianturco style zig zag Z stents on each of the tubular wall body portions 3, the tapering portions 6 and 7 and the reduced diameter portion 5 depending upon the overall length of the stent graft 1.

In the reduced diameter central portion 5 there is at least one substantially circular fenestration or aperture 13 on the tubular wall of the stent graft. In this embodiment there are three fenestrations being one for each of the two renal arteries and one for the superior mesenteric artery. Other numbers of fenestrations may also be used. The fenestrations 13 are substantially circular and extending from the fenestrations are tubular extensions 15. The tubular extensions 15 comprise a bio-compatible material tube 17 with a self expanding stent 19. In this embodiment the self expanding stent 19 is provided on the outer surface of the tubular extension but in an alternative embodiment the self expanding stent 19 may be provided on the inner surface of the graft material 17.

The biocompatible material tube 15 is a biocompatible graft material such as Dacron, Thoralon™, expanded PTFE material or a naturally occurring biomaterial, such as an extracellular matrix, such as small intestinal submucosa or other suitable material as previously identified.

Stitching 21 is provided to retain the tubular extension to the main graft.

Radiopaque markers 23 are provided at each end of the fenestration 13 at the base of the tubular extension 15 to assist a physician to locate the fenestration in respect to a side vessel extending from a main vessel. The radiopaque markers 23 may be gold or other convenient material.

Figure 4:
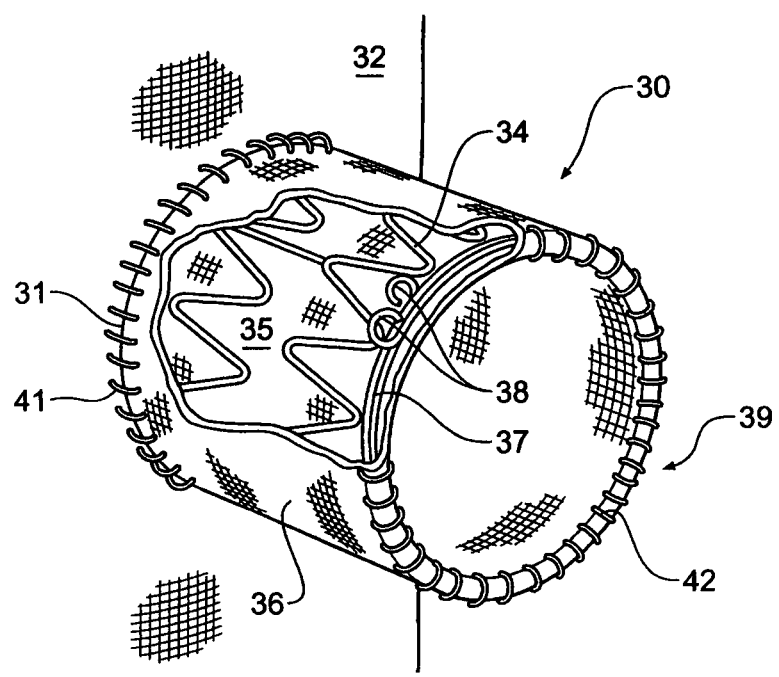
FIG. 4 shows a part cut away view of the embodiment shown in FIG. 3.

In the embodiment shown in FIGS. 3 and 4 the tubular extension generally shown as 30 extends from a fenestration or aperture 31 in the side wall of a main stent graft 32. The tubular extension 30 includes a self expanding Nitinol stent 34 with a bio-compatible graft material inner layer 35 and outer layer 36. A ring 37 of Nitinol around the periphery of the tubular extension at the terminal end 39 is provided to give good dimensional stability to the distal end of the tubular extension 30. In an alternative arrangement the ring 37 may be formed from stainless steel or any other convenient material. Stitching 41 is provided to retain the tubular extension to the main graft and stitching 42 is used to retain the ring 37 at the terminal end 39 of the tubular extension 30.

The ring 37 of Nitinol comprises two turns of wire with a loop 38 at each end of the wire. The loops 38 are provided to prevent the chance of damage to lumen wall because the pointed end of the wire is effectively enclosed within the loop.

It will be seen that by these various embodiments of this form of the invention that the tubular extension provides a good support and sealing surface into which another biocompatible material stent graft may be deployed to extend into a branch artery from a main artery or other lumen of the body.

Figure 5:
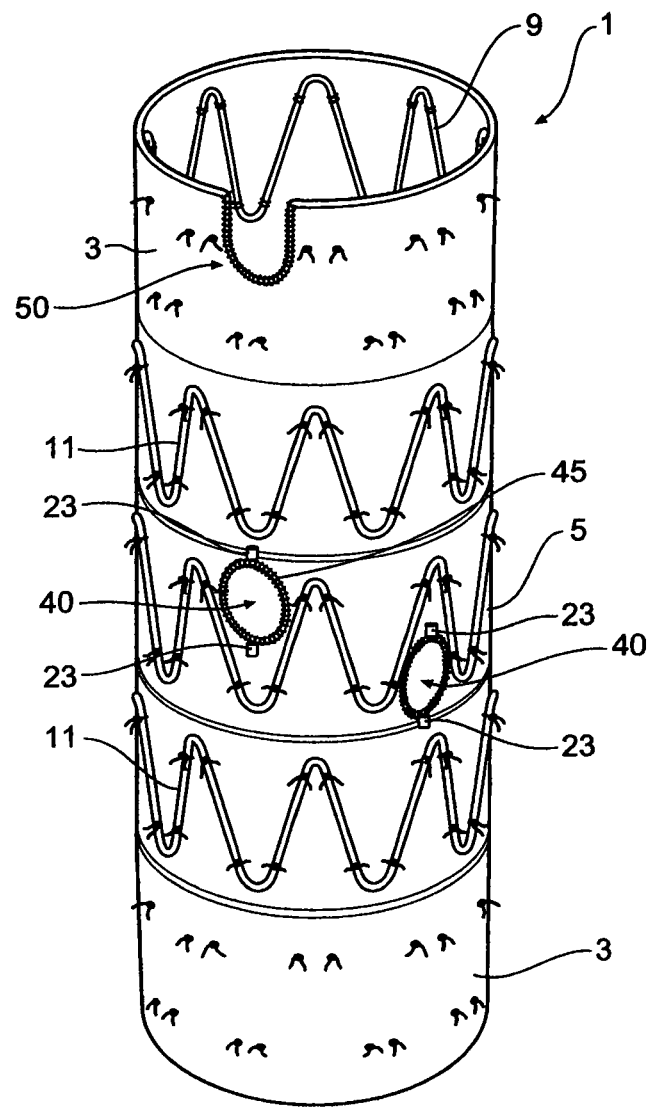
FIG. 5 shows an alternative embodiment of a stent graft according to this invention.
Figure 6:
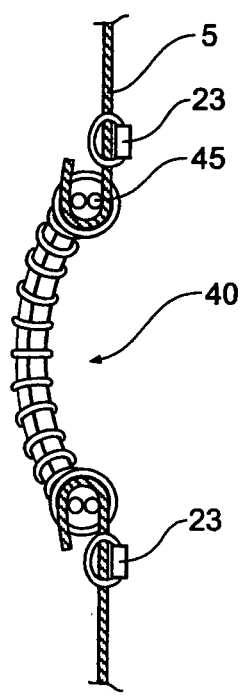
FIG. 6 shows a cross section through a fenestration shown in FIG. 5.
Figure 7:
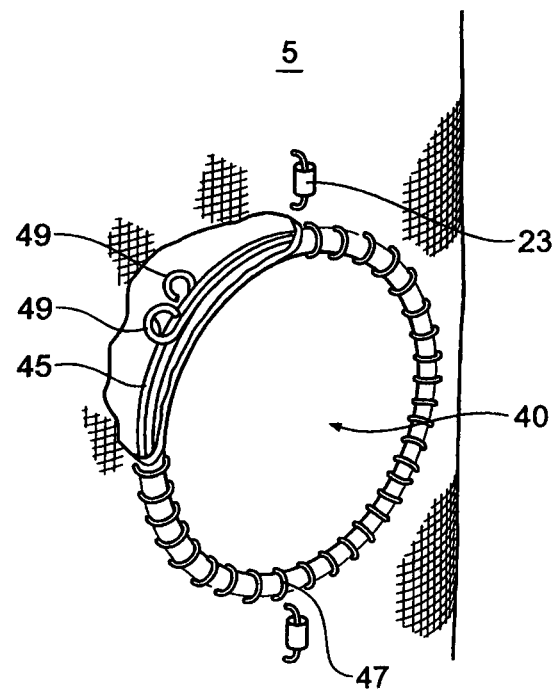
FIG. 7 shows a part cut away view of a fenestration of the embodiment shown in FIG. 5.

FIGS. 5 to 7 show an alternative embodiment of a stent graft according to this invention. In this embodiment the same reference numerals as used in FIG. 1 are used for corresponding components.

A main stent graft 1 comprises a tubular wall body portion 3 at proximal and distal ends of the stent graft 1 with a central tubular wall body portion 5.

All of the tubular wall body portions are a biocompatible graft material such as Dacron, Thoralon™, expanded PTFE material or a naturally occurring biomaterial, such as an extracellular matrix, such as small intestinal submucosa or other suitable material.

Gianturco style zig zag Z stents 9 are provided inside the graft material of the tubular wall body portions 3 at each end and on the central tubular wall body portion 5 Gianturco style zig zag Z stents 11 are provided on the outside of the graft material. There may be further Gianturco style zig zag Z stents on each of the tubular wall body portions 3 and the central tubular wall portion 5 than those illustrated depending upon the overall length of the stent graft 1.

In the central tubular wall body portion 5 there is at least one substantially circular fenestration or aperture 40 on the tubular wall of the stent graft. In this embodiment there are two fenestrations being one for each of the two renal arteries when this embodiment is deployed into the aorta. Other numbers of fenestrations may also be used where the placement of the stent graft involves the possibility of occluding other branch vessels such as the superior mesenteric artery. The fenestrations 40 are substantially circular. Radiopaque markers 23 are provided at each end of the fenestration 40 to assist a physician to locate the fenestration 40 in respect to a side vessel extending from a main vessel. The radiopaque markers 23 may be gold or other convenient material.

A ring 45 of Nitinol as can particularly be seen in FIGS. 6 and 7 is provided around the periphery of the fenestration 40 to give good dimensional stability to the fenestration 40. In an alternative arrangement the ring 45 may be formed from stainless steel or any other convenient material. Stitching 47 is provided to retain the ring 45 around the periphery of the fenestration 40.

The ring 45 of Nitinol preferably comprises at least two turns of wire with a loop 49 at each end of the wire. The loops 49 are provided to prevent the chance of damage to lumen wall because the pointed ends of the wire are effectively enclosed within the respective loops.

Alternatively one of the wires 45 may be a gold or other biocompatible heavy metal wire to provide radiographic visualisation of the ring to assist with positioning of the graft with respect to the branch vessel. Also in FIG. 5 there is shown a scalloped fenestration 50 which opens to the end 52 of the stent graft. Detail of the scalloped fenestration 50 can be seen in FIGS. 8 and 9.

Figure 8:
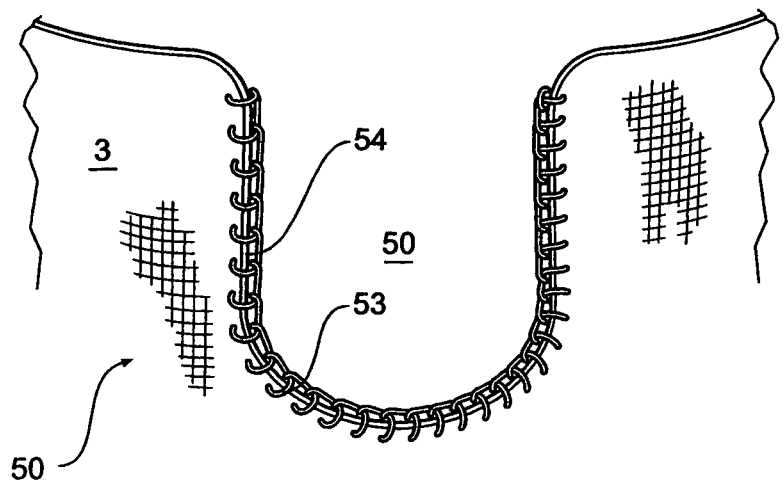
FIG. 8 shows a detailed view of the inside of a scalloped fenestration according to one embodiment of the invention.
Figure 9:
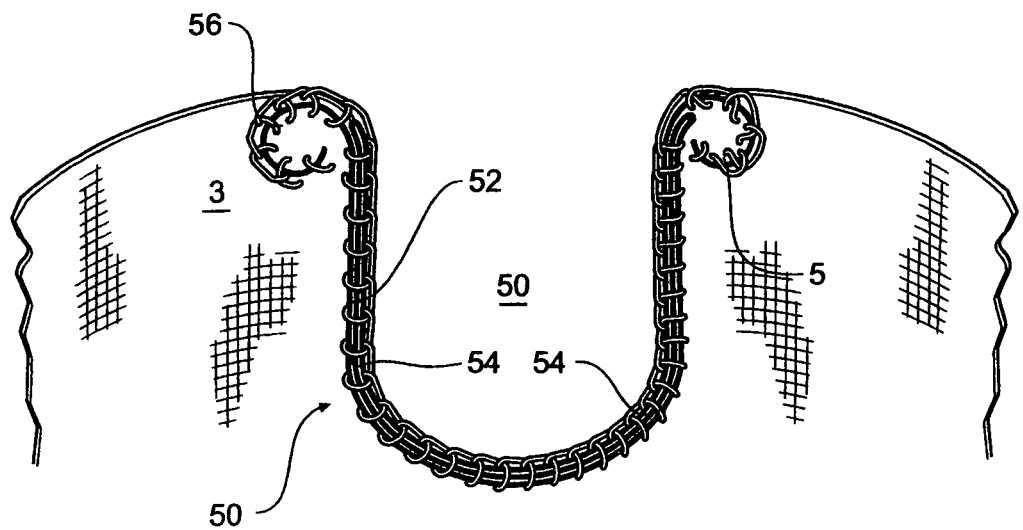
FIG. 9 shows an inside view of the embodiments shown in FIG. 8.

FIG. 8 shows an external view of a scalloped fenestration which can be placed at either the distal or proximal end of a stent graft and FIG. 9 shows an internal view of the fenestration shown in FIG. 8. The fenestration comprises a scallop of graft material cut out of the body of the graft 3. As can be seen in FIG. 9 an arch of resilient wire 52 is stitched around the periphery 54 of the scalloped fenestration. The wire 52 has a loop 56 formed at each end of it so that no sharp end of the wire is provided which could damage the wall of a vessel into which the stent graft is deployed. Because the wire or other material from which the U-shaped reinforcement 52 is resilient the fenestration will close up when the stent graft is in a contracted state for deployment into a bodily lumen such as the aorta and when released will open up to enable blood flow through the fenestration to a branch vessel.

The arch of resilient wire 52 is preferably made from a number of strands, such as three strands, of a resilient wire such as Nitinol. The wire is stitched to the periphery of the fenestration with stitches 53.

Figure 10:
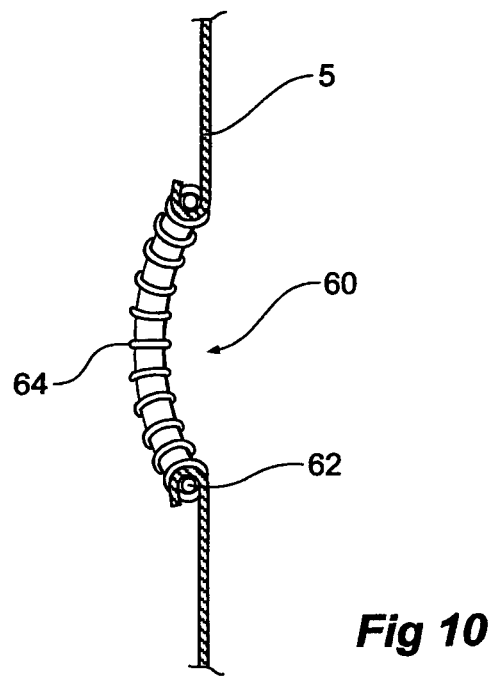
FIG. 10 shows an alternative embodiment of fenestration with a resilient elastomer ring surrounding the periphery of the fenestration.
Figure 11:
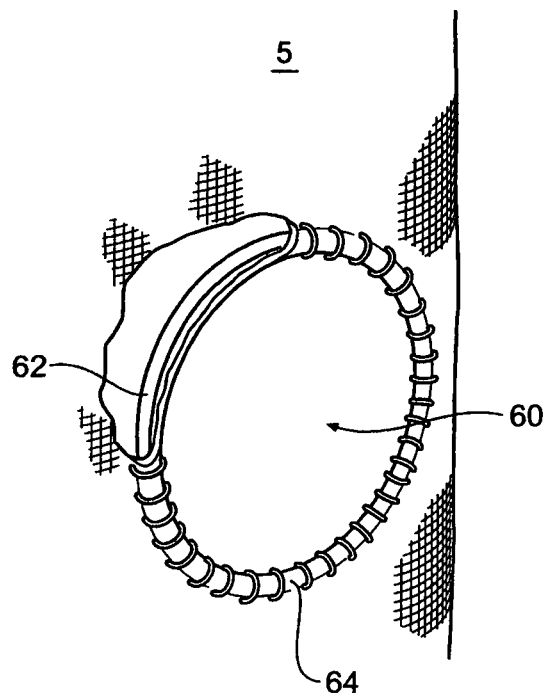
FIG. 11 shows another view of the embodiment of FIG. 10.

FIGS. 10 and 11 show two views of an alternative fenestration arrangement according to the invention. In this embodiment the fenestration 60 is provided in the tubular wall 5 of a stent graft and surrounding the fenestration 60 and providing reinforcement is an elastomeric ring 62 of a material such as silicon elastomer. The elastomeric ring 62 is sewn by stitching 64 into the periphery of the fenestration 60. Once again the elastomeric ring can be deformed so that it can be deployed within a deployment device and will open into the shape of the fenestration when deployed. The elastomeric ring will provide a certain amount of resiliency in position of the fenestration over a branch vessel and if deploying a side arm through the fenestration the elastomeric ring will provide a degree of blood sealing onto the branch stent graft.

FIGS. 12 and 13 show an alternative arrangement of fenestration on a stent graft. In FIG. 12 the stent graft 68 comprises a tubular wall body of graft material 70 with a lumen therethrough. The distal end 72 of the stent graft has distally extending exposed stent 74 and within the tubular wall body 70 there are proximal and distal internal stents 76 and 78 respectively and at least one external stent 80 intermediate the proximal distal ends. A fenestration is provided at the distal end 72 of the stent graft 68. In this embodiment the fenestration 82 is in the form of a scallop extending from the distal end 72 of the stent graft 68. The fenestration 82 is aligned with the struts 84 and 86 of the distal internal self expanding zig zag stent 78 so that the sides of the fenestration 90 can be stitched by stitching 92 to the struts 84 and 86 along at least part of their length.

Radiopaque or MRI opaque markers 94 are provided each side of the fenestration another marker 96 is provided at the base of the fenestration to enable visualisation of the fenestration to an accurate position with respect to a branch vessel such as a coeliac artery.

Once again, it will be noted that when the stent graft 68 is compressed for deployment within a delivery device the fenestration 82 will close up but upon release the fenestration will open to provide access to the branch artery.

FIG. 13A shows an alternative arrangement of a scalloped fenestration. In this embodiment the struts 93 and 95 of a zig-zag stent 97 are bent so that a more U-shaped fenestration 98 can be formed in the stent graft 99.

Figure 14:
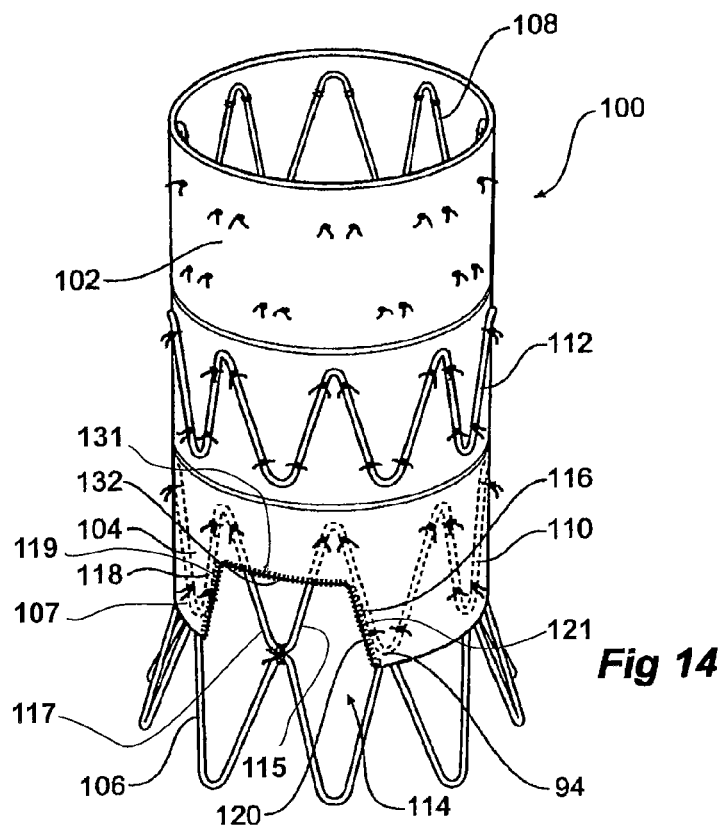
FIG. 14 shows an alternative embodiment of a stent graft with a scalloped fenestration.
Figure 15:
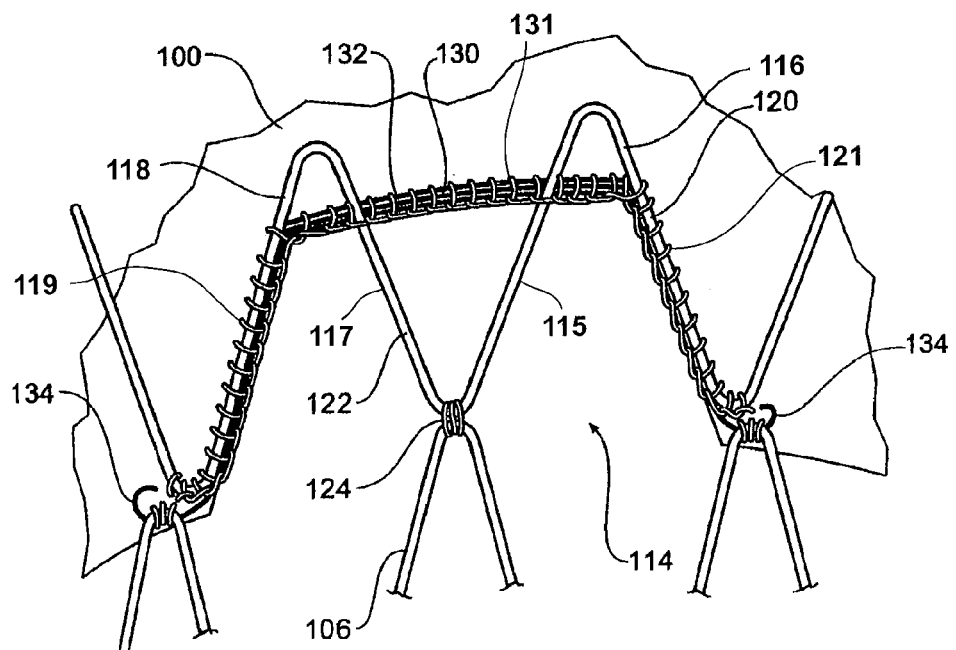
FIG. 15 shows a detailed internal view of the scalloped fenestration of FIG. 14.

FIG. 14 shows an alternative embodiment of a stent graft with a scalloped fenestration and FIG. 15 shows a detailed internal view of the scalloped fenestration of FIG. 14.

In FIG. 14 the stent graft 100 comprises a tubular wall body of graft material 102 with a lumen therethrough. The distal end 104 of the stent graft has distally extending exposed stent 106 and within the tubular wall body 102 there are proximal and distal internal stents 108 and 110 respectively and at least one external stent 80 intermediate the proximal distal ends. A fenestration is provided at the distal end 104 of the stent graft 100. Stent 107, shown here as an internal stent, comprises a plurality of struts. As shown, struts 117 and 118 comprise adjacent struts, and struts 115 and 116 comprise adjacent struts. In this embodiment the fenestration 114 is in the form of a scalloped fenestration extending from the distal end 104 of the stent graft 100 toward the proximal end 102 of the stent graft. The scalloped fenestration 114 has three sides 119, 121, and 131. Sides 119 and 121, as shown in FIGS. 12, 13, 13A, 14, 15 are substantially longitudinal, whereas side 131 is a substantially lateral side. As shown in FIGS. 14 and 15, the scalloped fenestration 114 is aligned with spaced apart struts 116 and 118 of the distal internal self expanding zig zag stent 110 so that the sides 119, 121, and 131 of the fenestration 114 can be stitched by stitching 120 to the struts 116 and 118 along at least part of their length. As shown in FIGS. 12, 13, 13A, 14 and 15, the stitching may be on some of the sides, all of the sides, or a portion of one or more of the sides. As shown in FIG. 14, zig-zag portion 122 of the distal internal self expanding zig zag stent 110 extends uncovered through the fenestration and suture 124 joins a bend of the distally extending exposed stent 106 to a bend of the distal internal self expanding zig zag stent 110. As FIGS. 14 and 15 show, the length of the lateral side 131 is greater than the minimum distance between any two adjacent struts, for example lateral side 131 has a length that is longer than the minimum distance between adjacent struts 115 and 116. This feature is also shown in FIGS. 12 and 13. As FIGS. 14 and 15 also show, the length of the lateral side 131 also may be greater than the maximum distance between adjacent struts.

The enlarged fenestration of this embodiment is illustrated as a double width as it takes in regions between two pairs of struts of the stent but may also be provided as a triple width. The enlarged fenestration enables a stent graft to be placed where there are several branch vessels in close proximity to each other which should not be occluded.

The scalloped fenestration shown in FIGS. 12 to 15 have been illustrated as being on the distal end of a stent graft but they may also be provided on the proximal end of a stent graft with or without the uncovered self expanding stent.

The use of a resilient reinforcement around the periphery of the fenestration provides a much more dimensionally stable aperture for the deployment of a leg or side arm extension. Particularly if using a balloon expandable stent as a leg or side arm extension is used the force of the balloon expansion will not tend to tear the graft material which may occur if no reinforcement was provided. The resiliency allows the fenestration to close off during contraction for deployment but to open up to a desired size and shape upon release in situ.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A stent graft comprising a tubular body defined by a tubular wall and comprising a first end and a second end, the tubular wall being formed from a biocompatible graft material and having an internal lumen and an internal wall, terminal self expanding stent portion disposed within the tubular lumen at the first end and abutting at least a portion of the internal wall, the internal terminal self expanding stent portion comprising struts and bends between the struts, only a single U shaped scalloped fenestration which is open at one side in the tubular wall provided at the first end of the tubular wall, the single scalloped fenestration including a periphery, the periphery extending between a pair of struts, the pair of struts at least partially defining the single U shaped scallop fenestration in the biocompatible graft material between the pair of struts, the biocompatible graft material being stitched to the pair of struts at least partially around the periphery of the single U shaped scalloped fenestration, whereby during deployment the bent struts of the internal terminal zig zag self expanding stent assist with opening up of the single U shaped scalloped fenestration into the U shape.

2. A stent graft as in claim 1 further including at least a second fenestration in the tubular wall intermediate the first end and the second end of the tubular body, the second fenestration including a second periphery and reinforcement around the second periphery, whereby the ring provides dimensional stability to the second fenestration to assist with sealing for deployment of a side arm extension therein.

3. A stent graft as in claim 2 wherein the reinforcement comprises a ring comprises at least two turns of the resilient wire.

4. A stent graft as in claim 3 wherein terminal ends of the resilient wire of the ring are provided with a loop, whereby the wire does not present a pointed end of wire which could damage a vessel.

5. The stent graph of claim 1 further comprising a second stent proximally adjacent the internal terminal stent and extending from the first end.

6. The stent graft of claim 1 wherein the stent has a distance between the pair of struts, as measured from one substantially longitudinal strut to the other substantially longitudinal strut, defining the single U shaped scalloped fenestration, and the distance between the pair of struts defining the single U shaped scalloped fenestration is greater than a distance between another pair of adjacent struts.

7. A stent graft comprising a tubular body of biocompatible graft material having:
- a proximal end, proximal end opening, and a proximal end opening edge,
- a distal end, a distal end opening, and a distal end opening edge,
- a lumen between the proximal end opening and distal end opening,
- an internal terminal stent disposed within the lumen of the stent graft distal of the proximal end opening such that the graft material at least partially encloses the stent within the lumen, and
- only a single scallop in the graft material at the proximal end of the graft material extending distally from the proximal end opening edge and having a periphery,
- wherein the internal stent comprises at least two struts that extends along, defines, and supports at least a portion of the periphery of the single scallop,
- wherein the internal stent comprises a self-expanding stent having apices and struts,
- wherein the single scallop is disposed between a pair of apices,
- wherein the distance between the pair of apices, as measured from apex to apex, is greater than a minimum distance between any other pair of apices that are adjacent to each other.

8. The stent graft of claim 7 further comprising at least one fenestration in the graft material.

9. The stent graft of claim 7 where the portion of the internal stent extending along and supporting the periphery of the single scallop is stitched to the periphery.

10. A stent graft comprising:
- a tubular body of biocompatible graft material,
- a first end and a first end opening,
- a second end and a second end opening,
- a lumen between the first and second ends,
- an internal terminal stent disposed within the lumen of at least one of the ends of the stent graft and at least partially covered by the graft material,
- only a single scallop in the graft material at one of the ends of the stent graft, the single scallop having a periphery,
- a first frame supporting at least a portion of the periphery of the single scallop,
- at least two fenestrations having a perimeter, separate from the single scallop, formed in the graft material, and
- each fenestration having a frame separate from the stent supporting at least a portion of the perimeter of each fenestration.

11. The stent graft of claim 10 wherein a portion of the internal terminal stent comprises the frame of the single scallop.

* * * * *